United States Patent
Fried et al.

(10) Patent No.: US 7,201,926 B2
(45) Date of Patent: Apr. 10, 2007

(54) ENVIRONMENTALLY SAFE INSECT REPELLENT COMPOSITION

(75) Inventors: Howard L Fried, New Rochelle, NY (US); Donna Khazan, New Brunswick, NJ (US); Mark N Morales, Staten Island, NY (US)

(73) Assignee: Bugaway Brands, L.L.C., Woodland Hills, CA (US)

( * ) Notice: Subject to any disclaimer, the term of this patent is extended or adjusted under 35 U.S.C. 154(b) by 0 days.

(21) Appl. No.: 11/087,389

(22) Filed: Mar. 22, 2005

(65) Prior Publication Data

US 2005/0249768 A1 Nov. 10, 2005

Related U.S. Application Data

(63) Continuation of application No. 10/162,009, filed on Jun. 4, 2002, now abandoned, which is a continuation-in-part of application No. 09/874,361, filed on Jun. 5, 2001, now abandoned.

(60) Provisional application No. 60/209,346, filed on Jun. 5, 2000.

(51) Int. Cl.
*A01N 65/00* (2006.01)
*A01N 55/00* (2006.01)
*A61K 36/00* (2006.01)

(52) U.S. Cl. .................. 424/725; 424/403; 424/747; 424/736

(58) Field of Classification Search ............... 424/725, 424/403, 732, 735, 736, 747, 776
See application file for complete search history.

(56) References Cited

U.S. PATENT DOCUMENTS

| | | | |
|---|---|---|---|
| 5,556,881 A | 9/1996 | Grahn Marisi | |
| 5,565,208 A | 10/1996 | Vlasblom | |
| 5,688,509 A | * 11/1997 | Radwan et al. | ............. 424/736 |
| 5,716,602 A | 2/1998 | Uick | |
| 5,792,465 A | 8/1998 | Hagarty | |
| 5,814,325 A | 9/1998 | Rod | |
| 6,548,085 B1 | 4/2003 | Zobitne et al. | |
| 2003/0039674 A1 | 2/2003 | Bessette | |

FOREIGN PATENT DOCUMENTS

WO    WO 96/35769    * 11/1996

OTHER PUBLICATIONS

Bowers et al., "Insect Repellents From the Chinese Prickly Ash *Zanthoxylum bungeanum*," Journal of Natural Products (Lloydia), 56(6):935-938 (1993) (abstract only).

Shukla et al., Insect Repellent Property of Essential Oils of Foeniculum-vulgare *Pimpinella-anisum* and Anethole, Pesticides (Bombay), 23(1):33-35 (1989) (abstract only).

* cited by examiner

*Primary Examiner*—Ruth A Davis
(74) *Attorney, Agent, or Firm*—Fish & Neave IP Group Ropes & Gray LLP

(57) ABSTRACT

An insect repellent composition containing citronella oil, D-limonene, 2 or more synergists, and 3 or more essential oils as the active ingredients. The preferred essential oils are geranium oil, rosemary oil and peppermint oil, but other essential oils may be used. In the preferred embodiment the synergists are aldehyde C-14 and aldehyde C-18. As desired, vanillin may be used as a stabilizer, and fragrances, fragrance enhancers and surfactants may be utilized.

20 Claims, No Drawings

ENVIRONMENTALLY SAFE INSECT REPELLENT COMPOSITION

CROSS REFERENCE TO RELATED APPLICATIONS

This is a continuation of U.S. patent application Ser. No. 10/162,009, filed Jun. 4, 2002, now abandoned, which was a continuation-in-part of application Ser. No. 09/874,361, filed Jun. 5, 2001, now abandoned, which claimed the benefit of U.S. Provisional Patent Application No. 60/209,346, filed Jun. 5, 2000.

FIELD OF THE INVENTION

The invention relates to insect repellents that may be topically applied and also used in manufacturing products with insect repellent capability, and primarily involves the use of citronella oil, D-limonene, two synergists and a plurality of essential oils as the active insect repellent component.

BACKGROUND OF THE INVENTION

Insects invade every walk of live, from the agricultural fields where our food is grown to the outdoor picnic to the garbage cans waiting for pickup. Billions of insects of many thousands of vanities swarm and fly all over every part of the globe every day. From the dawn of man, creative attempts have repeatedly been made to deal with this problem.

Both to protect crops and animals and maintain public health, many products have been offered over the years to combat insects. It is estimated that as much as ten percent of the food man produces is consumed by insects. In addition to being annoying, insects transmit innumerable diseases, some of which are fatal and can cause epidemics. Due to the present concern over insect-borne diseases, such as lyme disease carried by ticks and West Nile virus carried by mosquitoes, there is an ever increasing need for an environmentally friendly insect repellent, which is effective to repel insects As is well know, insects breathe by means of tubes that open at the body surface in spiracles. Internally, these tubes divide into very fine branches leading to the internal vital organs. These spiracles are water repellent, but oil may enter them. Accordingly, different types of oils are typically used to enter the spiracles and to damage the internal organs, so the insects will be killed or at least repelled.

There is an important distinction between insecticides and repellents. Insecticides are intended to destroy or kill insects, are generally much stronger than repellents and are toxic to man in varying degrees. Substantially most of the insecticides have to be registered by the Environmental Protection Agency (EPA), as they all typically have some level of toxicity. Many of these insecticides are not biodegradable and some (such as DDT) have been banned from agricultural use due to their harmful ecological effects.

Repellents, however may be defined as substances that cause an insect to turn away—"be repelled." They are necessarily milder, and are intended merely to "turn away" or "repel" insects, as opposed to actually destroying or killing them. Literally thousands of compositions are know to have some effect in repelling insects.

Essential oil are volatile oils derived from the leaves, stem, flower, or twigs of plants, and usually carrying the odor or flavor of the plant. They have a pungent taste and odor and generally are colorless. Over the years, they have been used widely in perfumery and flavors. Many of these essential oils have insect repellent capability, as is well known in the industry.

Many considerations are involved in creating insect repellents. Attention must be given to toxicity, biodegradability, ecological effect, harshness, skin dessication and skin and eye irritation, among another factors. Many repellents that are environmentally safe and friendly are harsh and are skin and eye irritants, whereas many that are safe for the body are not good for the environment.

In the past, little attention was given to the toxicity of compounds used to control insects. That is no longer the case. Strong control over these products is exercised by the U.S. Environmental Agency (EPA). Most insect repellents that are registered with EPA have warnings to prohibit their use near food or in food-serving places and in waters bearing fish, or that they cannot be applied to children.

It can, therefore, be appreciated that there is an ever growing market demand for environmentally safe insect repellents that actually effectively work to repel insects. The Food & Drug Administration (FDA) has a classification know as "GRAS," which designates "Generally Regarded As Safe" compounds. Certain essential oils follow into the GRAS category.

Citronella oil is a well-known and widely used insect repellent. The primary component responsible for its repellent properties is β-citronellol, 3,7-dimethyl-6-octen-1-ol, which is a member of the class of compounds known as terpenes.

D-limonene is another insect repellent, although not as well-known and widely used as citronella oil. D-limonene, 1-methyl-4-(1-methylethenyl)cyclohexene, is also a member of the terpene class.

Some insect repellents are on the market, wherein the active insect repellent is an essential oil, such as citronella oil. These products are generally very weak as repellents and have little effective usefulness. The most common effective insect repellents include DEET as the active compound, but these products are not ecologically friendly and are not natural; they also require EPA registration, and are now being limited in their human usage by the EPA.

Accordingly, there is a market demand for a natural insect repellent which is environmentally safe and friendly, as well as being safe for humans.

SUMMARY OF THE INVENTION

Therefore, it is an object of this invention to provide a natural insect repellent which effectively repels insects.

Another object is to provide an effective insect repellent which is environmentally safe and friendly.

A further object is to provide a safe insect repellent that does not cause any adverse effects on people.

These and other objects of the invention are obtained by an insect repellent, wherein the active ingredients are citronella oil, D-limonene, 2 synergists and 3 or more essential oils. A synergistic effect is thus created and the strength of the insect repellent is substantially increased over what could be obtained by using only a single essential oil, as is done in the industry.

Aldehydes may be used as the synergists to make the repellent more long lasting.

In a preferred embodiment a stabilizer, such as vanillin, may be used.

To improve the odor, one or more fragrances may be added.

While it is know to separately use citronella oil and D-limonene as the active ingredient in insect repellent compositions, it was not known that the strength of the composition can be synergistically increased by combining citronella oil and D-limonene with a plurality of essential oils. This is the inventive aspect of the invention. Further, the use of synergists, such as aldehydes, serve to increase the effective life of the insect repellent compound.

DETAILED DESCRIPTION OF THE INVENTION

The essence of this invention is that it utilizes citronella oil, D-limonene, 2 synergists and 3 or more essential oils as the active component of the insect repellent. This creates a far more effective repellent than was heretofore obtainable.

Combining essential oils together can create a synergistic effect, as opposed to an additive effect. In particular, using three essential oils together can be 10 to 15 times stronger than a repellent with only one essential oil. The use of 7 essential oils together can achieve a strength that is 15–30 times as strong as using just a single essential oil.

There are literally hundreds of essential oils. Not all of them can be combined together, however. Some essential oils have an antagonistic effect on each other when combined. Others do not have insect repellent capabilities.

In prior art repellents, if they used essential oils as active components, they used only a single essential oil. There are no insect repellents with multiple essential oils as the active ingredients.

Depending on the desired end use of the insect repellent composition, the composition can be formulated to be oil soluble, cationic water soluble or anionic water soluble.

For the preferred embodiment, geranium oil, rosemary oil and peppermint oil are combined to form one of the active insect repellent ingredients. Other essential oils that may be used are lavender oil, spearmint oil, pine needle oil and eucalyptus oil. Less suitable, but still effective are lemon oil, grapefruit oil, lavandin oil, cinnamon oil, clove oil, thyme oil, wintergreen oil, cedar oil, lemon grass oil, mandarin oil, tangerine oil, orange oil, citrus oil, lime oil, coriander oil, pomegranate oil, walnut oil, peanut oil, corn oil, canola oil, sunflower oil, sesame oil, linseed oil, safflower oil and olive oil.

In order to assure that the composition will be long lasting and that the oils will mix together synergistically, 2 or more synergists need to be used. For best results an aldehyde is used for this purpose, and, in particular, aldehyde C-14 (Dihydro-5-heptyl-2 (3H)— furanone, CAS No. 104-67-6) or aldehyde C-18 (Dihydro-5-pentyl-2 (3H)-furanone, CA No. 104-61-0). Other compositions that may be used are iso-bornyl acetate, N-amyl alcohol, devanaoil, nootkatone, litsea cubeba and benzoic acid. Very good results are achieved when aldehyde C-14 and aldehyde C-18 are used together.

To create the insect compound the essential oils may be dissolved in a terpene. These are unsaturated hydrocarbons occurring in most essential oils and oleoresins of plants. Best results are achieved with orange terpene. Though less suitable, effective results can also be obtained with lemon terpenes, mandarin terpenes, tangerine terpenes, lime terpenes, and grapefruit terpenes.

In another preferred composition, 7 essential oils are dissolved in a terpene. Preferably, geranium oil, rosemary oil, peppermint oil, lavender oil, spearmint oil, pine needle oil and eucalyptus oil are used, but any essential oil with insect repellent characteristics may be used, such as some of the above listed essential oils. While any terpene may be used, best results are achieved with orange terpene. Below are the preferred percentages by weight of the components for such an insect repellent composition

|  | Acceptable | Preferable | Best |
| --- | --- | --- | --- |
| D-limonene | 1.0–15.0% | 1.6–11.4% | 2.0–8.9% |
| Citronella oil | 0.1–20.0% | 1.5–15.0% | 3.0–5.0% |
| Geranium oil | 0.5–25.0% | 1.0–15.0% | 1.5–9.5% |
| Rosemary oil | 0.1–12.5% | 0.3–9.5% | 0.4–9.0% |
| Peppermint oil | 0.1–10.0% | 0.5–5.0% | 1.0–1.5% |
| Lavender oil | 0.1–17.0% | 0.5–12.5% | 2.0–6.0% |
| Spearmint oil | 0.5–22.5% | 1.0–15.0% | 2.0–6.5% |
| Pine needle oil | 0.5–18.5% | 0.75–9.5% | 1.0–5.0% |
| Eucalyptus oil | 0.1–5.5% | 1.5–4.0% | 2.0–3.5% |
| Terpene | 15.0–75.0% | 22.5–60.0% | 25.0–60.0% |

To make the insect repellent composition, at room temperature (20° C.), each essential oil and also the citronella oil and D-limonene are slowly mixed into the terpene mixture until it is completely dissolved. A standard laboratory beaker with a magnetic stirring bar may be used.

A stabilizer may be used to keep the insect repellent mixture from changing its form or chemical nature. Vanillin has been found effective for this purpose and may be used. In the above example, there should be between 0.01–12.5& by weight of stabilizer. The preferred range is 0.25–9.5% and best results are obtained with 0.5–5.5%.

To make 5 pounds of this insect repellent compound, start with 3 pounds (60%) of orange terpene. 0.15 pounds (3%) of the stabilizer (usually vanillin) is slowly dissolved at room temperature in the terpene until a paste is created. Then each essential oil, the citronella oil and D-limonene, one at a time, are slowly mixed into the mixture at room temperature until it is completely dissolved. It does not matter in which order the oils are dissolved. In this example, use 0.25 pounds (5%) of citronella oil, pounds (%) of D-limonene, 0.4 pounds (8%) of geranium oil, 0.15 pounds (3%) of rosemary oil, 0.25 pounds (5%) of peppermint oil, 0.2 pounds (4%) of lavender oil, 0.25 pounds (5%) of spearmint oil, 0.25 pounds (5%) of pine needle oil, and 0.1 pounds (2%) of eucalyptus oil.

As is common in many insect repellents, fragrances may be used to mask the pungent odor of the essential oils and to make the repellent smell more pleasing. Best results are obtained with neroli oil and anethole, but other useful fragrances are rose oil, violet extract, mandarin oil, methylionone, sandal wood, musk and patchouly.

To bring out the best effects of the fragrance, a fragrance enhancer, such as citral, heliotropine, aldehyde C-10, linalool or oil petigrain mandarin can be used.

To better assure a synergistic, harmonious composition, a carrier may be used. Among the compositions that may be used are citral, pinene, camphene, lavandin oil, terpineol and linalool. Though not as suitable, water, mineral oil, and soybean oil can be effectively used.

Surfactants are compounds that reduces surface tension when dissolved in water or water solutions, or which reduces the interfacial tension between two liquids, or between a liquid and a solid. In some applications, surfactants, such as sodium lauryl sulfate or polysorbate 80 may provide beneficial improvements on the insect repellent composition.

EXAMPLE 1

A standard 500 ml laboratory beaker is used with a magnetic stirring bar. 1.40 g of vanillin are first dissolved in 41.93 g of orange terpene, followed by dissolving 0.29 g of heliotropine and 0.29 g of anethole. Then, the remaining elements were dissolved into the oil soluble composition. This composition included the following ingredients:

|  | Weight percentage |  | Weight percentage |
| --- | --- | --- | --- |
| citronella oil | 3.25% | d-limonene | 4.54% |
| aldehyde C-14 | 0.40% | aldehyde C-18 | 0.39% |
| lavender oil | 4.17% | spearmint oil | 3.47% |
| peppermint oil | 1.16% | iso-bornyl acetate | 0.95% |
| geranium oil | 4.16% | vanillin | 1.40% |
| anethole | 0.29% | heliotropine | 0.29% |
| pine needle oil | 2.24% | aldehyde C-10 | 0.59% |
| linalool | 2.68% | rosemary oil | 0.76% |
| citral | 1.13% | piperitone | 0.10% |
| lemon oil | 4.39% | grapefruit oil | 4.46% |
| N-amyl alcohol | 0.06% | lavandin oil | 8.58% |
| spike lavander | 2.19% | oil petigrain mandarin | 1.50% |
| eucalyptus oil | 0.31% | orange terpenes | 41.93% |
| terpineol | 4.41% | neroli oil | 0.20% |

The resulting oil soluble composition had a pale yellow color and a specific gravity at 25° C. of 0.8580 g/ml. Additionally, the refractive index of the composition at 20° C. was 1.4720 and it exhibited a peak absorbance of 0.420 at 345 nm. The flash point of the composition was determined to be 130° F.

EXAMPLE 2

The cationic water soluble composition corresponding to the composition of Example 1 was prepared using the same weight percentages of the components with the exception that the amount of orange terpene was reduced to 39.93 weight percent. The remaining 2.00 weigh percent was made up by the addition of Tween 80 (polysorbate 80) solution.

The resulting cationic water soluble composition had a pale yellow color and a specific gravity at 25° C. of 0.8523 g/ml. Additionally, the refractive index of the composition at 20° C. was 1.4713 and it exhibited a peak absorbance of 0.375 at 345 nm. The flash point of the composition was determined to be 115° F.

EXAMPLE 3

The anionic water soluble composition corresponding to the composition of Example 1 was prepared using the same weight percentages of the components with the exception that the amount of the orange terpenes was reduced to 39,93 weight percent. The remaining 2.00 weight percent was made up by the addition of sodium lauryl sulfate.

Into a standard laboratory beaker (500 ml) equipped with a magnetic stirring bar powder vanillin !1.40 g) was introduced into orange terpene (39.93 g). Then heliotropine (0.29 g) and anethole (0.29 g) were added and the solution was mixed until the powders were completely dissolved. The remaining components, with the exception of the sodium lauryl sulfate, were then added to the stirring solution. A portion of the resulting mixture, approximately 25% by volume, was removed and the powdered sodium lauryl sulfate was added to this portion with stirring.

After the sodium lauryl sulfate was completely dissolved, the portion containing the sodium lauryl sulfate was added back into the composition and mixed to yield the anionic water soluble composition.

The resulting anionic water soluble composition had a pale yellow color and a specific gravity at 25° C. of 0.8523 g/ml. Additionally, the refractive index of the composition at 20° C. was 1.4713 and it exhibited a peak absorbance of 0.375 at 345 nm. The flash point of the composition was determined to be 115° F.

EXAMPLE 4

The composition of Example 1 was applied to the exposed forearm of a human subject and the forearm placed inside an enclosed cage 12 inches×12 inches×12 inches filled with approximately 1,000 ordinary house flies. Similarly, in another exercise a similar concentration of OFF!® containing 14.24% N,N-diethyl-meta-toluamide (DEET), 0.75% related isomers, and 85% insert ingredients was applied to the forearm. In a third exercise, the forearm was untreated. The untreated arm showed no repellency zone and the flies were much more highly disturbed by the presence of the arm treated with the composition of Example1. Off!® repelled flies from landing on the treated area of the arm and, to some degree, on the cage nearby. This zonal effect began to dissipate after one hour, with some flies landing and immediately taking off during the second hour post treatment and actually walking briefly over the treated arm during the third hour. On the arm treated with the composition of Example 1, it repelled flies from landing on the treated arm and on the cage nearby. The flies were greatly agitated by the presence of the composition, especially during the first hour. The zonal effect was pronounced even three hours after treatment of the arm

EXAMPLE 5

The composition of Example 1 was tested against a similar concentration of DEET, as described in Example 4, with the exception that mosquitoes were in the enclosed space, instead of house flies. Again, fewer flies landed on the forearm with the Example 1 composition.

EXAMPLE 6

The composition of Example 1 was homogeneously mixed with molten paraffin wax in an amount equal to 6% the Example 1 composition and 94% wax and poured into a mold containing a standard candle wick. When burned, the candle was found to repel insects for the entire life of the candle. 1,000 active adult house flies were released in a room ten feet by ten feet and eight feet high. All fans and ventilation were turned off. The flies were allowed to settle for 5 minutes. One candle was placed on a 4 foot high filing cabinet and It. Within 5 minutes many of the flies were agitated, cleaning themselves repeatedly with their forelegs and flying about actively. Those that found the ajar door, exited rapidly. Within 15 minutes 20% of the flies had exited the door and the remaining flies were all very active, and the candle fragrance became more pronounced. After 30 minutes, 33% of the flies had exited the door, and the fragrance of the candle had become very distinct throughout the room. After 60 minutes, all but 20–50 flies had exited the door, and the aroma of the candle was becoming quite strong.

EXAMPLE 7

The composition of Example 3 was homogeneously mixed into a paper slurry in an amount equal to 6% by weight before the slurry was pressed into sheets. Then, the resulting sheets were formed into disposable, paper tablecloths. These tablecloths were found to repel insects for a period of 24 hours. The tablecloths were found to have an extended shelf life if stored in standard plastic packaging until the time of use.

EXAMPLE 8

The composition of Example 2 was homogeneously mixed into a screen printing ink in an amount equal to 6% by weight. Then, the insect repellent ink was used to make screen printed T-shirts. These T-shirts were found to repel insects for an extended period of time and after several washings. The T-shirts were found to have an extended shelf life if stored in standard plastic packaging until the time of use.

EXAMPLE 9

The candle of Example 6 was made in two varieties, one with 3% of the instant insect repellent composition and another with 1.5%. In addition, the test was run with a 3% Citronella candle and with an unscented control candle. A three foot cubic enclosure was built and a candle was left inside for one hour. Then, 150 3–5 day old adult female mosquitoes were released. A 4–5 day old chick was placed in the cage. The candle with 3% of the instant composition was significantly better than the 3% Citronella candle and even the candle with 1.5% of the instant composition worked better than Citronella. The chicks were checked at the stated intervals for new bites and the cumulative number of bites was also recorded. The instant invention with the same concentration as Citronella produced 58% fewer bites and with half the concentration of Citronella even worked slightly better that Citronella.

| Time minutes | 3% Invention | | 1.5% Invention | | 3% Citronella | | Unscented | |
|---|---|---|---|---|---|---|---|---|
| | # Bites | Cum | # Bites | Cum | # Bites | Cum | # Bites | Cum |
| 0 | 0 | 0 | 0 | 0 | 0 | 0 | 0 | 0 |
| 5 | 3 | 3 | 6 | 6 | 7 | 7 | 19 | 19 |
| 10 | 3 | 6 | 8 | 14 | 8 | 15 | 16 | 35 |
| 15 | 4 | 10 | 10 | 24 | 12 | 27 | 9 | 44 |
| 30 | 5 | 15 | 9 | 33 | 6 | 33 | 13 | 57 |
| 45 | 3 | 18 | 4 | 37 | 4 | 37 | 7 | 64 |
| 60 | 1 | 19 | 4 | 41 | 8 | 45 | 11 | 75 |

EXAMPLE 10

The 3% candles from Test 9 were again used and compared to an unscented candle in the same environment. After the candle burned for an hour, 100 2–4 day old female mosquitoes were released. A 1–2 day old chick was place in the environment. The elapsed time as monitored until 15 mosquitoes bit the chick. It took 97 seconds for the unscented candle and 8 minutes for the 3% Citronella candle. When the candle with the 3% invention composition was used, it took 102 seconds for the unscented candle and 23 minutes for the candle with the inventions' composition. This shows that it took nearly 3 times longer for the chick to receive the same number of bites when the invention was used, as compared to Citronella.

EXAMPLE 11

Another test was conducted with the invention formulated as an aerosol and compared to OFF!® SKINTASTIK IV with 7% DEET and SKIN-SO-SOFT® bug guard plus IR 3535.3 newly hatched chicks were placed in the top well of a one cubic foot cage and exposed to 100 1-week old adult mosquitoes for 60 minutes in 15 minute increments. The number of mosquitoes is recorded, along with the landing at stated intervals, the total landings and the percentage of mosquitoes that landed.

| Product | # mosquitoes | 0–1 min | 15–16 min | 30–31 min | 45–46 min | 60–61 | Total | % land |
|---|---|---|---|---|---|---|---|---|
| Untreated | 75 | 8 | 3 | 6 | 3 | 4 | 24 | 32.0 |
| Invention | 75 | 0 | 0 | 0 | 1 | 2 | 3 | 4.0 |
| OFF | 40 | 0 | 0 | 0 | 2 | 1 | 3 | 7.5 |
| Skin-So-Soft | 40 | 3 | 2 | 1 | 3 | 4 | 13 | 32.5 |

The Invention performed almost twice as effectively as OFF with DEET, even when exposed to almost twice as many mosquitoes.

The invention is described in detail with reference to a particular embodiment, but it should be understood that various other modifications can be effected and still be within the spirit and scope of the invention.

We claim:

1. An insect repellent composition comprising as active ingredients: citronella oil; D-limonene; N-amyl-alcohol; 1 or more synergists selected from the group consisting of iso-bornyl acetate, davana oil and nootkatone; geranium oil; rosemary oil; and peppermint oil.

2. An insect repellent composition according to claim 1, further comprising a terpene.

3. An insect repellent composition according to claim 2, wherein the terpene is selected from the group consisting of orange terpenes, lemon terpenes, mandarin terpenes, tangerine terpenes, lime terpenes and grapefruit terpenes.

4. An insect repellent composition according to claim 1, further comprising a stabilizer.

5. An insect repellent composition according to claim 4, wherein said stabilizer is vanillin.

6. An insect repellent composition according to claim 1, further comprising a fragrance.

7. An insect repellent composition according to claim 6, wherein the fragrance is selected from the group consisting of neroli oil, anethole, rose oil, violet extract, mandarin oil, methylionone, sandal wood, musk and patchouli.

8. An insect repellent composition according to claim 6, further comprising a fragrance enhancer.

9. An insect repellent composition according to claim 7, further comprising a fragrance enhancer.

10. An insect repellent composition according to claim 8, wherein the fragrance enhancer is selected from the group consisting of citral, heliotropin, aldehyde C-10, linalool and oil petitgrain mandarin.

11. An insect repellent composition according to claim 9, wherein the fragrance enhancer is selected from the group consisting of citral, heliotropin, aldehyde C-10, linalool and oil petitgrain mandarin.

12. An insect repellent composition according to claim 1, further comprising a surfactant.

13. An insect repellent composition according to claim 12, wherein the surfactant is selected from the group consisting of sodium lauryl sulfate and polysorbate 80.

14. An insect repellent composition according to claim 1, further comprising a terpene, a stabilizer, a fragrance and a fragrance enhancer.

15. An insect repellent composition according to claim 14, wherein the terpene is selected from the group consisting of orange terpenes, lemon terpenes, mandarin terpenes, tangerine terpenes, and lime terpenes, wherein said stabilizer is vanillin, wherein the fragrance is selected from the group consisting of neroli oil, anethole, rose oil, violet extract, mandarin oil, methylionone, sandal wood, musk and patchouli, and wherein the fragrance enhancer is selected from the group consisting of citral, heliotropin, aldehyde C-10, linalool and oil petitgrain mandarin.

16. An insect repellent composition according to claim 14, further comprising a surfactant.

17. An insect repellent composition according to claim 16, wherein the surfactant is selected from the group consisting of sodium lauryl sulfate and polysorbate 80.

18. An insect repellent composition according to claim 15, further comprising a surfactant.

19. An insect repellent composition according to claim 18, wherein the surfactant is selected from the group consisting of sodium lauryl sulfate and polysorbate 80.

20. An insect repellent composition according to claim 1, wherein the composition comprises N-amyl alcohol and iso-bornyl acetate.

* * * * *